(12) United States Patent
Hentges et al.

(10) Patent No.: US 8,734,805 B2
(45) Date of Patent: May 27, 2014

(54) SYSTEMS AND METHODS FOR HARVESTING ALGAE FROM PHOTOBIOREACTORS

(75) Inventors: Peter F. Hentges, Fort Collins, CO (US); Thomas Carroll Barlow, Loveland, CO (US); Jeff Tyler Penoyer, Fort Collins, CO (US); David Scott Gorham, Hollis, NH (US); Jason Charles Quinn, Fort Collins, CO (US); Peter Allen Letvin, Fort Collins, CO (US); Christopher Wayne Turner, Windsor, CO (US); Guy Robert Babbitt, Fort Collins, CO (US); Nicholas Paul Echter, Wheat Ridge, CO (US); James William Howland, Littleton, CO (US)

(73) Assignees: Solix Biosystems, Inc., Fort Collins, CO (US); Colorado State University Research Foundation, Fort Collins, CO (US)

(*) Notice: Subject to any disclaimer, the term of this patent is extended or adjusted under 35 U.S.C. 154(b) by 1 day.

(21) Appl. No.: 12/822,117

(22) Filed: Jun. 23, 2010

(65) Prior Publication Data

US 2011/0120070 A1    May 26, 2011

Related U.S. Application Data

(60) Provisional application No. 61/220,136, filed on Jun. 24, 2009.

(51) Int. Cl.
*A61K 36/02* (2006.01)
*A01D 44/00* (2006.01)
*C12N 1/12* (2006.01)

(52) U.S. Cl.
CPC .. *A61K 36/02* (2013.01); *C12N 1/12* (2013.01)
USPC .......................... 424/195.17; 56/8; 435/257.1

(58) Field of Classification Search
CPC ............................... A61K 36/02; A61K 36/05
See application file for complete search history.

(56) References Cited

FOREIGN PATENT DOCUMENTS

| WO | 2008134010 A2 | 11/2008 |
|----|---------------|---------|
| WO | WO 2008134010 A2 * | 11/2008 |
| WO | 2009090549 A2 | 7/2009 |
| WO | WO 2009090549 A2 * | 7/2009 |

OTHER PUBLICATIONS

International Search Report and Written Opinion issued in PCT/US2010/039709, mailed Sep. 3, 2010, 9 pages.

* cited by examiner

*Primary Examiner* — Chris R Tate
*Assistant Examiner* — Russell Fiebig
(74) *Attorney, Agent, or Firm* — Faegre Baker Daniels LLP (57) ABSTRACT

A method for harvesting algae according to embodiments of the present invention includes filling a reservoir at least partially with a liquid, submerging a bag at least partially in the liquid, the bag containing media, the media comprising algae, the bag comprising a first end, a second end, a harvesting port located closer to the first end than to the second end, and a gas port, delivering gas into the bag through the gas port, and raising the second end of the bag by accumulating the gas at the second end to flow the media toward the harvesting port.

20 Claims, 5 Drawing Sheets

SYSTEMS AND METHODS FOR HARVESTING ALGAE FROM PHOTOBIOREACTORS

CROSS-REFERENCE TO RELATED APPLICATIONS

This application claims the benefit of U.S. Provisional Patent Application Ser. No. 61/220,136, filed on Jun. 24, 2009, which is incorporated by reference herein for all purposes.

TECHNICAL FIELD

Some embodiments of the present invention relate generally to algae harvesting, and more specifically to algae harvesting from film photobioreactor bags.

BACKGROUND

Removing algae from photobioreactors for harvesting and eventual processing, such as, for example, biofuels processing, often involves complex, time-consuming, and costly mechanisms. Pumps, as well as mechanical systems designed to mechanically squeeze algae or algae-containing media from a photobioreactor often use large amounts of energy, thereby increasing the cost of algae harvesting and/or biofuels production.

SUMMARY

A method for harvesting algae according to embodiments of the present invention includes filling a reservoir at least partially with a liquid; submerging a bag at least partially in the liquid, the bag containing media, the media comprising algae, the bag including a first end, a second end, a harvesting port located closer to the first end than to the second end, and a gas port; delivering gas into the bag through the gas port; and raising the second end of the bag by accumulating the gas at the second end to flow the media toward the harvesting port. An embodiment of the method may further include tethering the bag to the reservoir closer to the first end than to the second end. In some cases, the bag includes an elongated support member, and tethering the bag to the reservoir includes tethering the elongated support member to the reservoir. Tethering the elongated support member to the reservoir may include pivotally coupling the elongated support member to the reservoir. Raising the second end may include raising the second end up to an upper level of the liquid in the reservoir.

Methods for harvesting algae according to embodiments of the present invention may further include arranging multiple submerged bags in the reservoir and emptying different bags at different times or in different ways. For example, methods for harvesting algae according to embodiments of the present invention may include emptying every second bag simultaneously and re-submerging them before emptying the remaining bags.

A system for harvesting algae according to embodiments of the present invention includes a reservoir at least partially filled with a liquid; a media bag containing media, the media including algae, the bag at least partially submerged in the liquid, the bag including a first end and a second end and a harvesting port located closer to the first end than to the second end; and an inflation bag, the inflation bag coupled to the media bag and located closer to the second end than to the first end. In some cases, the inflation bag may be separate from the media bag.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
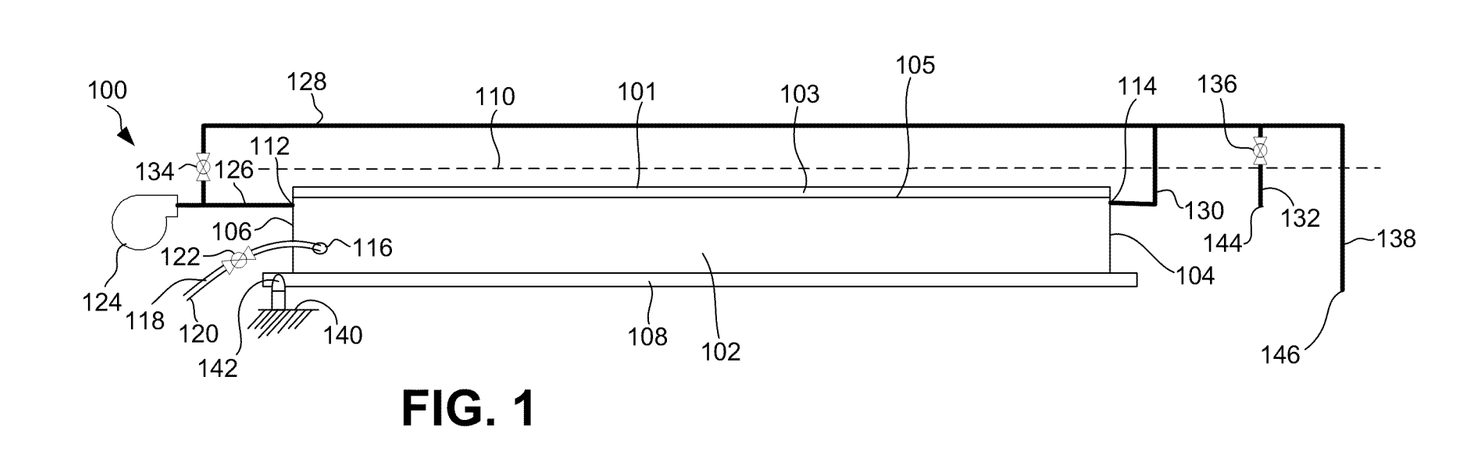
FIG. 1 illustrates a side elevation view of a photobioreactor and algae-harvesting system, according to embodiments of the present invention.
Figure 2:
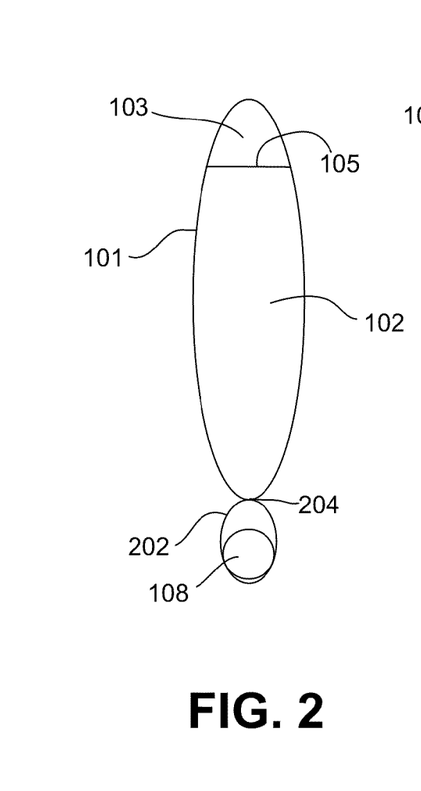
FIG. 2 illustrates a cross-sectional view of a photobioreactor bag, according to embodiments of the present invention.

FIG. 1 illustrates a side elevation view of a photobioreactor bag 101 and algae-harvesting system 100, according to embodiments of the present invention. FIG. 2 illustrates a cross-sectional view of a photobioreactor bag 101, according to embodiments of the present invention. The photobioreactor bag 101 includes a media 102 which may include water and/or algae or other microorganisms, and a head space 103 above the media within the bag 101, which may include air, carbon dioxide, and/or other gases, according to embodiments of the present invention. The bag 101 may also be coupled to a weight member 108 via a weight member interface 202; the weight member interface 202 may be a channel and/or one or more loops formed in the bag 101 and configured to receive a weight member 108. Weight member 108 may be a pipe or other device for providing weight to the bag 101 to prevent the bag from moving and/or floating to the top due to the buoyancy created by the gases in the head space 103, according to embodiments of the present invention. Weight member 108 may be a PVC pipe filled with concrete, or other sufficiently stiff and/or heavy ballast material, according to embodiments of the present invention. Weight member interface 202 may be formed by welding the sides of the bag 101 together at location 204, for example. According to some embodiments of the present invention, weight member 108 is a pipe or strut, such as a pipe with a weight of approximately three hundred forty pounds per one hundred feet.

As used herein, the term "coupled" is used in its broadest sense to refer to elements which are connected, attached, and/or engaged, either directly or integrally or indirectly via other elements, and either permanently, temporarily, or removably. As used herein, the term "pivotally coupled" is used in its broadest sense to refer to elements which are coupled in a way that permits one element to pivot with respect to another element. As used herein, the terms "fluidly coupled" or in "fluid communication" are used in their broadest sense to refer to elements which are coupled in a way that permits fluid flow between them.

The bag 101 may be at least partially submerged in a reservoir, the bottom of which is indicated at least partially at reference numeral 140, and the top level of the liquid (e.g. water) in the reservoir is indicated by reference numeral 110, according to embodiments of the present invention. The reservoir may be any natural or artificial container capable of holding liquid, according to embodiments of the present invention. The bag 101 includes a harvesting port 116, and a harvesting tube 118 in fluid communication with the bag 101 via the harvesting port 116, according to embodiments of the present invention. The harvesting tube 118 may also include a valve 122 which, during harvesting, may be opened to permit the media 102 within the bag 101 to flow toward the harvesting port 116, through the harvesting tube 118, and out of the end 120 of the harvesting tube 118. The harvested media may then be stored and/or further processed to separate the algae from the water, for example, for further processing steps.

As illustrated in FIG. 1, the weight member 108 may be coupled with the bag 101 along some or all of the length of the bag, from one end 104 of the bag 101 to another end 106 of the bag 101, according to embodiments of the present invention. The weight member 108 may be coupled to the reservoir 140 or other underlying surface; for example, the weight member 108 may be pivotally coupled to the reservoir 140 at location 142, according to embodiments of the present invention. According to some embodiments of the present invention, the weight member 108 may be pivotally coupled to the reservoir 140 with a zip tie connection or the like.

A blower 124 is in fluid communication with the bag 101 via line 126, according to embodiments of the present invention. Another line 128 fluidly connects the blower 124 with another end 104 of the bag 101 via line 130. Line 128 may be referred to as a filler bypass line, according to embodiments of the present invention. Exhaust lines 132 and 138 are also in fluid communication with lines 126, 128, and 130, according to embodiments of the present invention. Line 126 is in fluid communication with the bag 101 via gas inlet port 112, and line 130 is in fluid communication with the bag 101 via gas exhaust port 114, according to embodiments of the present invention. Although port 112 is shown as being located toward end 106 and port 114 is shown as being located toward end 104, one of ordinary skill in the art, based on the disclosure provided herein, will recognize the various other possible locations of ports 112 and/or 114. Valve 134 is located inline between pump 124 and line 128, and valve 136 is located inline between line 128 and line 132, according to embodiments of the present invention.

During normal operation, valve 134 is closed and blower 124 blows gas through line 126, into gas inlet port 112, and into the photobioreactor bag 101, according to embodiments of the present invention. The gas may be carbon dioxide, air, and/or a mixture of gases. For example, blower 124 may blow air into the bag 101 to provide a certain air pressure sufficient to maintain a desired head space 103 and thus maintain the photobioreactor bag 101 in an upright position submerged within the reservoir or tank 140. During normal operation, valve 136 is open, and because end 144 of line 132 is under the liquid (e.g. water) level 110, the blower 124 supplies the air to the bag 101 at or above the pressure at end 144 in order to maintain the head space 103. If blower 124 supplies air at a flow rate sufficient to raise the pressure in the bag 101 higher than the pressure at the depth of end 144, air will flow through the bag 101 and exhaust out of end 144. In such a scenario, the air will not exhaust out of end 146 of line 138 because end 146 is at a greater depth, and thus a higher pressure, than end 144. This normal operating pressure may be, for example, equivalent to three or four inches of water (e.g. the end 144 may be three or four inches below level 110).

During a harvesting operation, valve 134 is opened and valve 136 is closed. This causes the air supplied by the blower 124 to reach a higher pressure before exhausting, because the closure of valve 136 requires a higher pressure within the line 128 and photobioreactor bag 101 before the air exhausts through end 146, according to embodiments of the present invention. The air (and/or combination of gases) from blower 124 accumulates within the bag 101 and the end 104 begins to raise toward the surface level 110, according to embodiments of the present invention. According to some embodiments of the present invention, the harvesting port 116 is located closer to end 106 than end 104 so that, as gas accumulates at the second end 104, the end 104 is raised, thus flowing the media 102 toward the harvesting port 116.

According to some embodiments of the present invention, the harvesting cycle may be initiated in different ways. For example, in some systems, line 132 and valve 136 may be eliminated, and the pressure at the end of line 138 may be varied between a normal operating pressure and a harvesting pressure (e.g. the pressure at which gas accumulates to raise the bag 101) by mechanically moving the end 146 from a normal operating depth below level 110 to a deeper, harvesting depth below level 110. This may be done, for example, by building line 138 as a PVC pipe extending through a frictional gasket or grommet, whose vertical position with respect to the water level 110 may be adjusted by manually lifting up or pushing down on the line 138, according to embodiments of the present invention.

Figure 3:
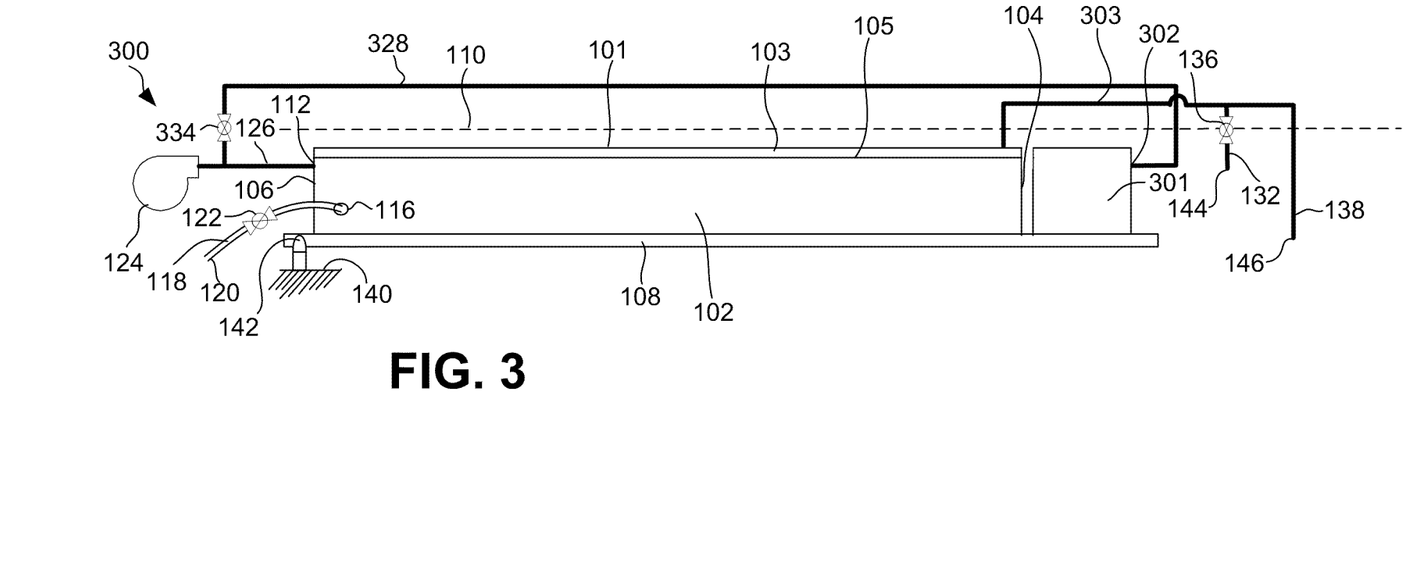
FIG. 3 illustrates a side elevation view of a photobioreactor and alternative algae-harvesting system, according to embodiments of the present invention.

FIG. 3 illustrates a side elevation view of a photobioreactor 101 and alternative algae-harvesting system 300, according to embodiments of the present invention. During normal operation of system 300, valve 334 is closed, and blower 124 blows air (or any other gas or mixture of gases) into bag 101, and the air exhausts through line 303 out of end 144, which is submerged below level 110 to pressurize the head space 103. According to some embodiments of the present invention, level 144 is at the same distance below level 110 as level 105 is below 110. Valve 334 is inline with line 328 which is in fluid communication with flotation bag 301 via gas port 302, according to embodiments of the present invention. According to some embodiments of the present invention, the flotation bag 301 is separate from the photobioreactor bag 101 (e.g. is not in fluid communication with bag 101), but may also be coupled to weight element 108 and/or bag 101, according to embodiments of the present invention. During a harvesting operation, valve 334 is opened and valve 136 is closed, which causes inflation of bag 301, causing end 104 to rise toward the surface level 110, according to embodiments of the present invention. This raising of end 104 and the pressure difference between end 144 and end 146 causes enhanced accumulation of gas inside the bag 101 near end 104, which in turn further raises the bag 101 and directs media 102 flow toward the harvesting port 116, according to embodiments of the present invention. Once the harvesting operation is complete, the inflation bag 301 may be deflated through an exhaust line (not shown), and valve 334 may be closed, to permit re-submergence of the bag 101, according to embodiments of the present invention.

An exhaust port for the inflation bag 301 may be included in several different ways. For example, valve 334 may be a three-way valve which fluidly couples blower 124 with line 328 during harvesting and fluidly couples line 328 with an exhaust line or atmosphere during a deflation of bag 301, according to embodiments of the present invention. Alternatively, the bag 301 may include one or more small leak orifices formed therein, such that gas within the bag 301 leaks out of bag 301 more slowly than the rate at which blower 124 can supply gas to the bag 301. This permits the bag 301 to fill when connected with blower 124, while also permitting the bag to slowly deflate when blower 124 is turned off or disconnected, according to embodiments of the present invention. Based on the disclosure provided herein, one of ordinary skill in the art will recognize various other ways to exhaust bag 301.

Figure 4:
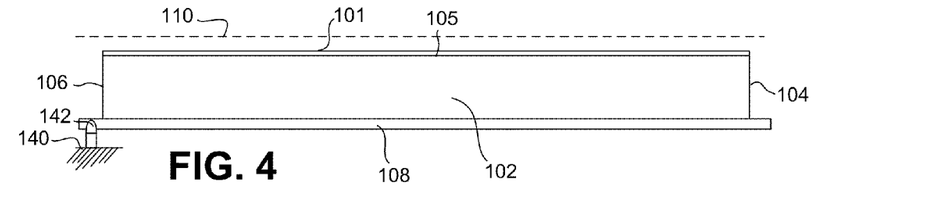
FIG. 4 illustrates a side elevation view of a submerged photobioreactor bag and algae-harvesting system prior to harvesting, according to embodiments of the present invention.

FIGS. 4-7 illustrate side elevation views of the photobioreactor bag 101 of FIG. 1 in various stages during a harvesting operation, in which the blower 124, lines 126, 128, 130, 132, and the harvesting line 118 are omitted from the drawings for clarity, according to embodiments of the present invention. As shown in FIG. 4, the bag 101 begins submerged under water level 110, due to the weight of the weight member 108 offsetting the buoyancy force created by the head space 103 and the bag 101, according to embodiments of the present invention.

Figure 5:
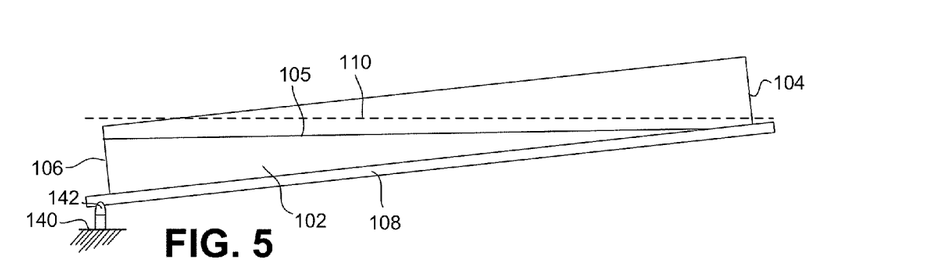
FIG. 5 illustrates the photobioreactor bag of FIG. 4 during a harvesting procedure, according to embodiments of the present invention.

Once the valve 134 is opened and valve 136 closed, the end 104 of the bag 101 begins to accumulate air and floats further toward the top surface 110, as illustrated in FIG. 5. According to some embodiments, this occurs when the buoyancy force of the air within the bag 101 exceeds the weight of the bag 101 and the weight member 108. As shown in FIG. 5, the weight member, or support member, 108 is pivotally coupled to pivot 142, which permits end 104 to rise while leaving end 106 submerged. When the end 104 rises toward and eventually floats at or above the water level 110 in the tank or reservoir 140, the difference in height between end 104 and end 106, and/or the dynamic motion of the end 104 swinging upward toward the surface 110, creates a "dumping" effect which causes flow of the media 102 from end 104 toward end 106, and thus toward the harvesting port 116 near or at end 106, according to embodiments of the present invention. Furthermore, if any media 102 within the bag 101 were to end up above the water level 110, enough media 102 will be displaced within the bag to cause the media level 105 to lower to a level at or near the surface liquid level 110, according to embodiments of the present invention. Such media 102 will be displaced by draining through harvesting port 116, according to embodiments of the present invention.

Figure 6:
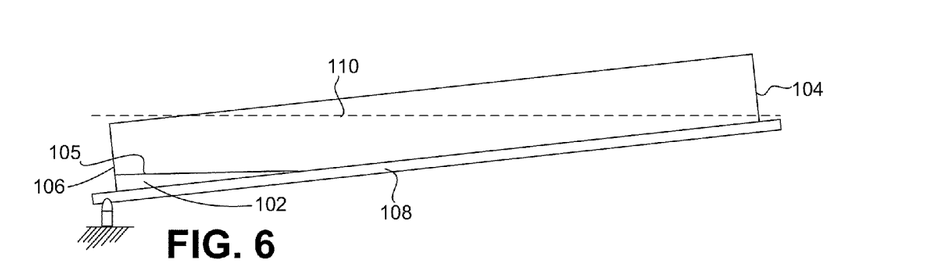
FIG. 6 illustrates the photobioreactor bag of FIGS. 4 and 5 during a harvesting procedure, according to embodiments of the present invention.

During or after the gravitational and/or dynamic "dumping" and fluid displacement occurs, the bag 101 begins to fill with air until the pressure within the bag 101 reaches the pressure at the depth of end 146 of exhaust line 138, according to embodiments of the present invention. As illustrated in FIG. 6, the air accumulates within the bag 101 and increases the air pressure within the bag 101, thereby displacing the media 102 below the surface level 110 and pushing it out of harvesting port 116. Placing the end 146 of the exhaust line 138 at a depth at or below the depth of the harvesting port 116 from the surface 110 may enhance this air displacement effect during harvesting, because the air pressure in the bag 101 will build up to a degree sufficient to displace the media 102 until the depth difference between the media level 105 and the surface level 110 is at or near the depth difference between the end 146 and the surface level 110 (due, for example, to the pressure of the water in the reservoir surrounding the bag 101), according to embodiments of the present invention.

Placing the end 120 of the harvesting tube 118 at an atmospheric depth below the harvesting port 116 and/or the bottom of the bag 101 (or at a pressure otherwise lower than the pressure at the harvesting port 116) may enhance the harvesting process by creating a siphon effect for outward flow of media 102 through the harvesting line 118, according to embodiments of the present invention. According to some embodiments of the present invention, a vacuum source such as, for example, a shop vac, may be placed in fluid communication with end 120 of harvesting tube 118 to enhance the siphoning or pressure differential effect, to facilitate harvesting. According to some embodiments of the present invention, the same pump or blower 124 used to blow gas into the bag 101 may also be used, simultaneously for example, to create a suction or negative pressure on the harvesting tube 118.

Figure 7:
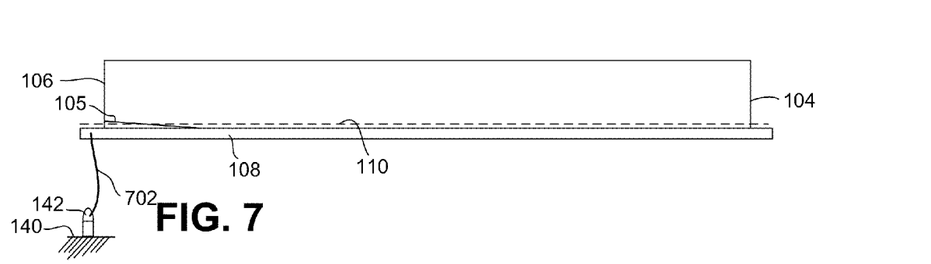
FIG. 7 illustrates the photobioreactor bag of FIGS. 4-6 during a harvesting procedure, according to embodiments of the present invention.

According to alternative embodiments of the present invention, the weight member 108 may be releasably tethered to pivot 142 by a tether line 702, which permits the entire end 106 of the bag 101 to float to the surface 110, as illustrated in FIG. 7. The tether line 702 may instead be a mechanical linkage, such as, for example, a single bar pivotably coupled to base 142 and weight member 108, according to embodiments of the present invention. Using a tether line or linkage may further enhance the gravitational displacement effect and require less air pressure for the harvesting process (e.g. lower depth of end 146 and/or lower power blower 124), according to embodiments of the present invention. According to some alternative embodiments of the present invention, the linear weight density of the weight member 108 varies between ends 104 and 106, such that the weight member 108 is heavier toward end 106 and remains at or near the bottom 140 of the tank throughout the harvesting process while permitting end 104 to rise, even with or without a connection or tethering between weight member 108 and bottom 140. According to some embodiments of the present invention, the linear weight density of the weight member 108 varies between ends 104 and 106, such that the weight member 108 is heavier toward end 106 and remains at or near the bottom 140 of the tank throughout the harvesting process while permitting end 104 to rise, until the media 102 is almost completely drained from the bag 101, at which point the buoyancy of the bag 101 lifts the entire weight member 108 toward the surface (similar to that depicted in FIG. 7).

Once the media 102 has been drained and/or harvested from within the bag 101, and/or once the bag 101 is empty or near empty, the bag 101 may be lowered back to the normal operating position by closing valve 134 and opening valve 136 to permit the accumulated air to exhaust through exhaust line 132, according to embodiments of the present invention. The bag 101 may be refilled with media 102 such as, for example, through harvesting port 116 and/or through another port. The refilling of the bag 101 with media 102 may be done while the bag 101 is sinking back toward the bottom 140 of the tank to speed up the sinking process, or it may be added after the bag 101 is back to its original position, according to embodiments of the present invention.

Figure 8:
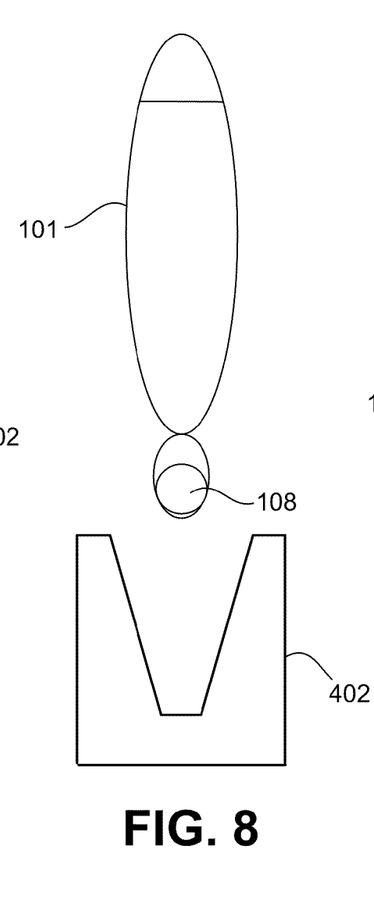
FIG. 8 illustrates a cross-sectional view of a photobioreactor bag and alignment groove with the photobioreactor bag in a raised position, according to embodiments of the present invention.
Figure 9:
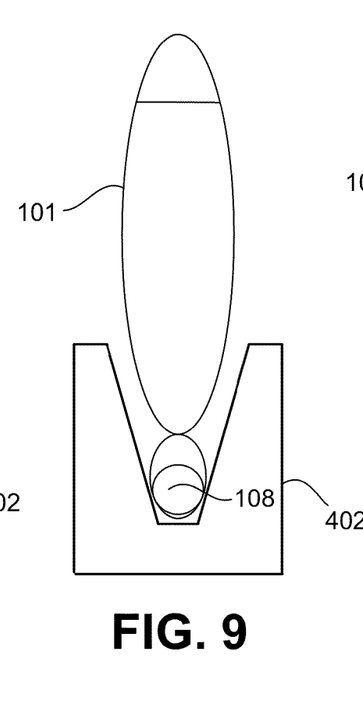
FIG. 9 illustrates a cross-sectional view of a photobioreactor bag and alignment groove with the photobioreactor bag in a lowered position, according to embodiments of the present invention.
Figure 10:
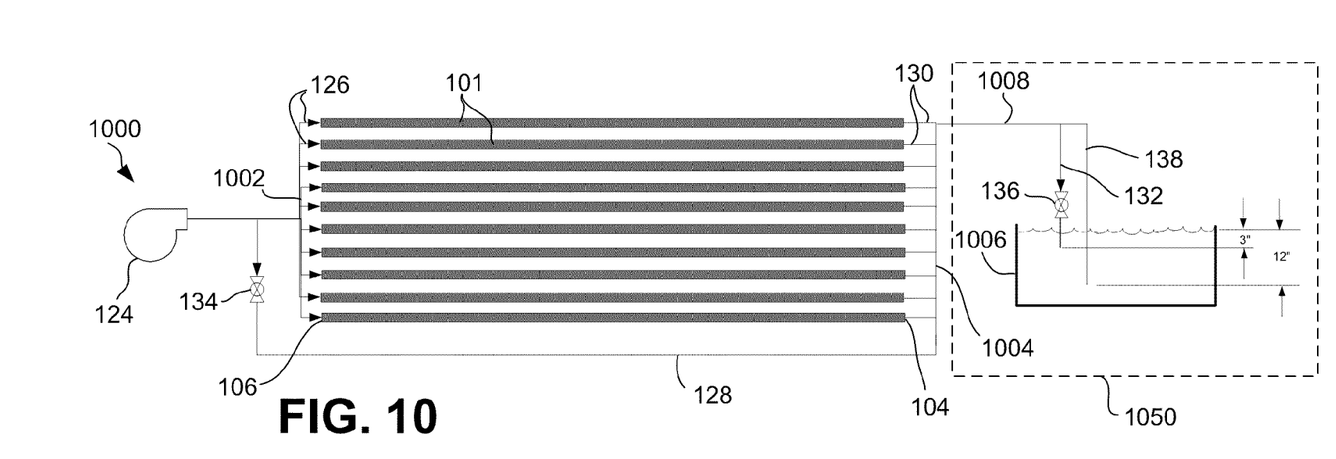
FIG. 10 illustrates a combined partial top view and partial side view of a series of photobioreactor bags and an algae harvesting system, according to embodiments of the present invention.
Figure 11:
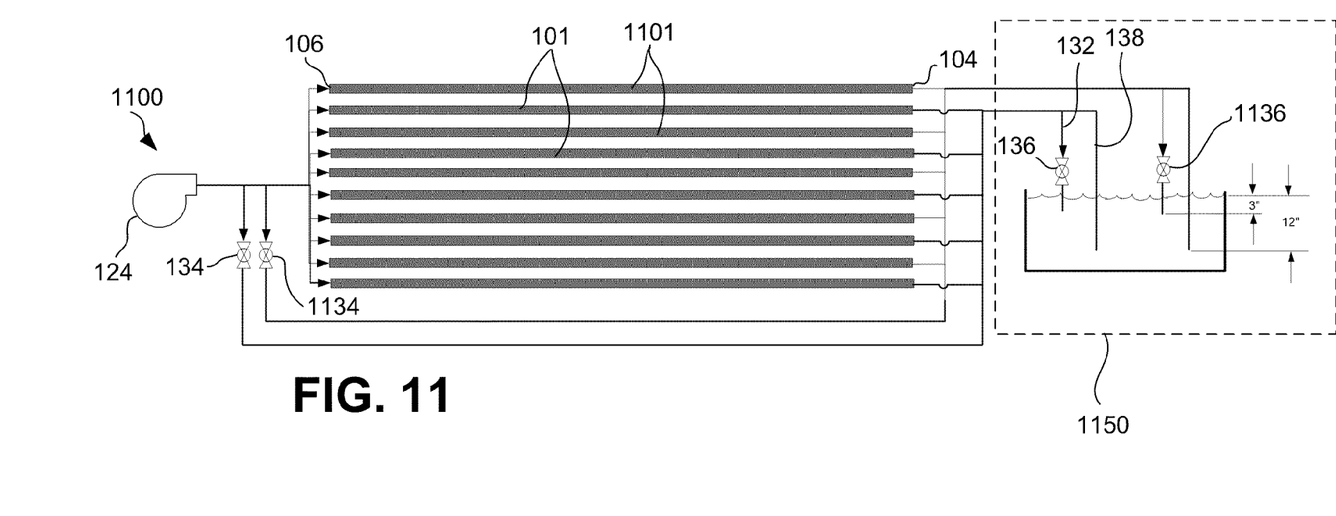
FIG. 11 illustrates a combined partial top view and partial side view of a series of photobioreactor bags and an alternative algae-harvesting system, according to embodiments of the present invention.

As illustrated in FIGS. 8 and 9, a guide device 402 may be used below the weight member 108 and photobioreactor bag 101 to guide the bag 101 back into a desired position as it sinks. Multiple guide devices 402 (or a continuous guide groove or guide device) may be used along the length of, or at intervals along the length of, the weight member 108 from end 104 toward end 106, according to embodiments of the present invention. Multiple guide devices 402 may also be used in parallel to guide more than one bag 101 back into place where the bags 101 are arranged in multiples next to each other, as illustrated in FIGS. 10 and 11. A linkage attached to the bottom of bag 101 and/or weight member 108 further assists the bag 101 in descending to its original or desired position, according to embodiments of the present invention.

According to some embodiments of the present invention, the bag 101 remains coupled with the bottom 140 of the reservoir along its length, and remains partially or wholly submerged throughout the harvesting process. Such a harvesting process may be accomplished by adding gas to the inside of the bag 101 to achieve a pressure that is high enough to push the media level 105 down and push the media 102 out of the harvesting tube 118, according to embodiments of the present invention. According to other embodiments of the present invention, a combination of pressurizing of the inside of the bag 101 and floating the bag 101 upwards towards surface 110 may be used.

FIG. 10 illustrates a combined partial top view and partial side view of a series of photobioreactor bags 101 connected in parallel and an algae harvesting system 1000, according to embodiments of the present invention. The exhaust system 1050 is shown in partial side view in FIG. 10. The bags 101 may be arranged in parallel in a tank (not shown) to maximize production and harvesting density, according to embodiments of the present invention. Algae harvesting system 1000 is capable of initiating the harvesting process of multiple bags 101 simultaneously. A common gas header 1002 connects each gas inlet line 126, and a common exhaust header 1004 connects each exhaust line 130, according to embodiments of the present invention. Line 1008 connects the header 1004 with exhaust system 1050, which includes the exhaust lines 132 and 138. Exhaust lines 132 and 138, as described above, extend to different depths within tank 1006, which may in some embodiments be the same tank in which the photobioreactor bags 101 are submerged, according to embodiments of the present invention. As described above with respect to FIGS. 1 and 4-6, during normal operation valve 134 is closed and valve 136 is opened, and during harvesting, valve 134 is opened and valve 136 is closed.

FIG. 11 illustrates a combined partial top view and partial side view of a series of photobioreactor bags 101, 1101 and an alternative algae-harvesting system 1100, according to embodiments of the present invention. The exhaust system 1150 is shown in partial side view in FIG. 11. Bags 101 and 1101 are arranged in parallel similarly to the bags 101 of FIG. 10; however, two different back end systems permit the staggered harvesting of different groups of bags. During normal operation, valves 134 and 1134 are closed, and valves 136 and 1136 are open, and each bag 101 and 1101 operates as described with respect to FIG. 1. To harvest bags 101, valve 134 is opened and valve 136 closed. To harvest bags 1101, valve 1134 is opened and valve 1136 is closed. Harvesting adjacent bags in a staggered fashion may permit a higher degree of precision in returning the bags 101 and 1101 to their original starting positions and locations; for example, the bags 101 on either side of bag 1101 act as a kind of guide as bag 101 is deflated and permitted to sink back to its original position. Harvesting adjacent bags in a staggered fashion may also have less of an impact on the overall liquid level in the tank, and/or may facilitate harvesting with a harvesting tube 118 that has a limited flow rate, according to embodiments of the present invention.

Staggered and/or selective harvesting may also permit different bags to be harvested in different stages of algae growth and/or at different times. For example, bags 101 may contain an algae culture that is ready for harvesting, while bags 1101 may contain a young algae culture that still needs to grow. Although system 1100 is shown for staggered harvesting of two sets of bags 101, 1101, one of ordinary skill in the art will appreciate that more than two sets of bags may be configured for staggered and/or selective harvesting, according to embodiments of the present invention. According to some embodiments of the present invention, one bag 101 at a time is selected for initiation of a harvesting cycle.

Figure 12:
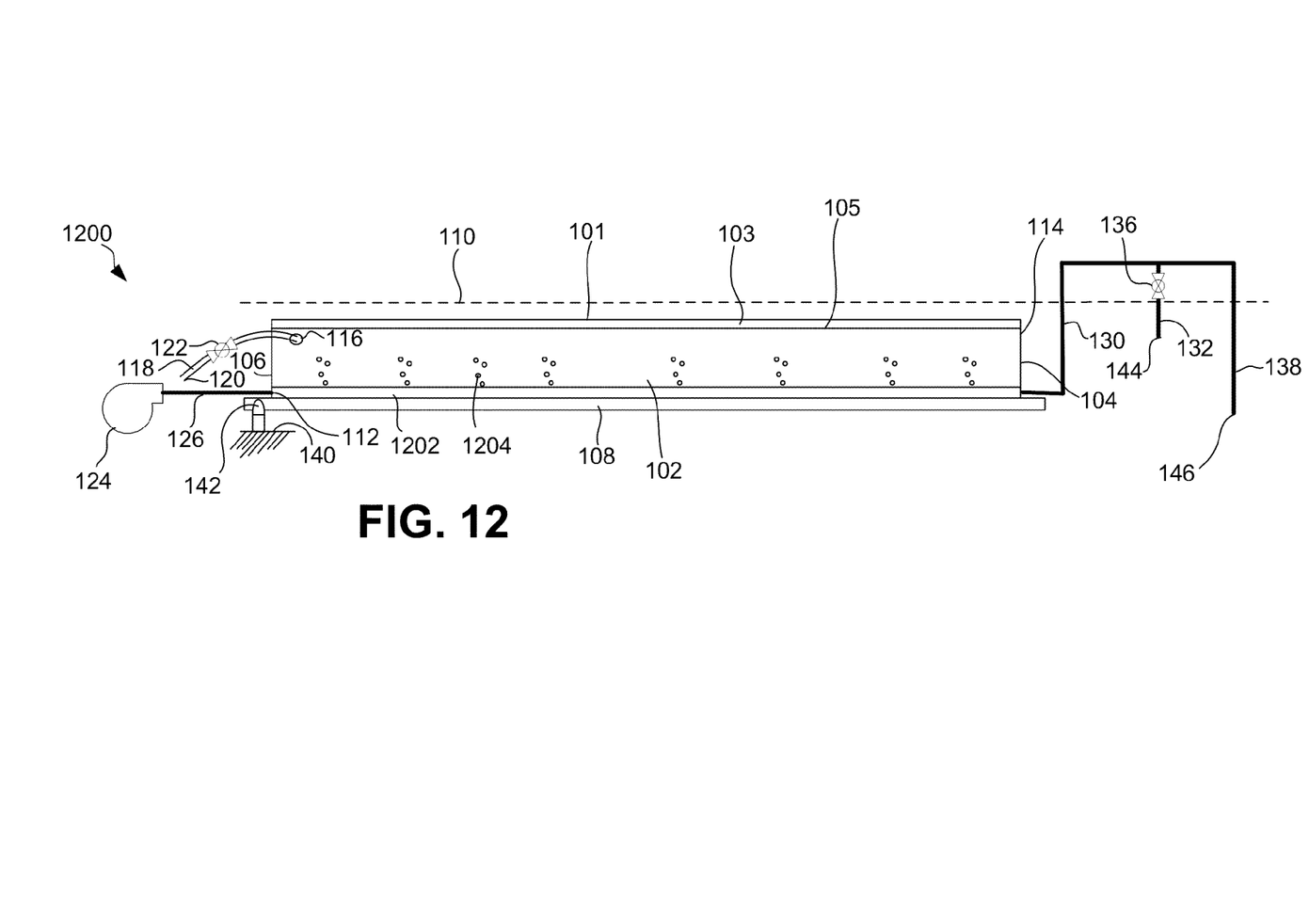
FIG. 12 illustrates a side elevation view of an alternative photobioreactor and algae-harvesting system, according to embodiments of the present invention.
Figure 13:
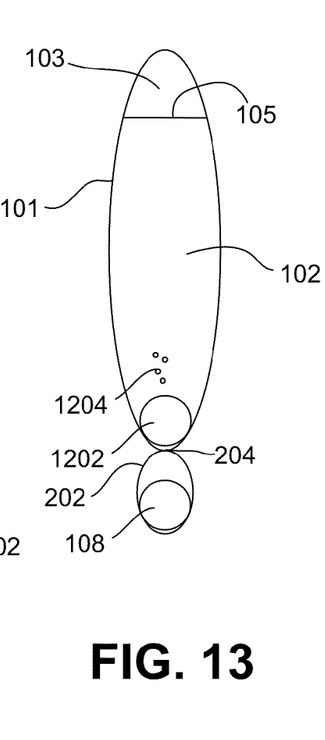
FIG. 13 illustrates a cross sectional view of the photobioreactor of FIG. 12, according to embodiments of the present invention.

FIG. 12 illustrates a side elevation view of an alternative photobioreactor and algae-harvesting system 1200, according to embodiments of the present invention. System 1200 is similar to system 100. However, in system 1200, line 128 is absent. System 1200 further includes a sparge tube 1202, which may be a separate tube or formed integrally with bag 101, and which is configured to deliver gas from blower 124 into the media 102 via bubbles 1204, according to embodiments of the present invention. The gas bubbles 1204 may be delivered through apertures formed or cut into an outer surface of the sparge tube 1202, according to embodiments of the present invention. Line 126 fluidly couples blower 124 with sparge tube 1202, and line 130 is in fluid communication with another end of the sparge tube 1202, according to embodiments of the present invention. FIG. 13 illustrates a side cross sectional view of system 1200, according to embodiments of the present invention.

To initiate a harvesting cycle, valve 136 is closed, thereby increasing the pressure at the end of the sparge tube 1202 nearest end 104, and thereby causing the delivered gas 1204 to accumulate in the head space 103. The accumulated gas eventually creates a buoyancy force which lifts end 104 toward the surface 110, thereby causing the media 102 to begin flowing out of the harvesting tube 118, as described with respect to FIGS. 4-7, according to embodiments of the present invention. Line 128 (see FIG. 1), while optional, may be helpful in situations in which the flow rate of gas from the sparge tube 1202 into media 102 is not sufficient to cause a sufficiently rapid accumulation of gas within the bag 101.

Although some embodiments of the present invention include pressure regulation systems that involve lines 132, 138 submerged to different depths under water in order to control the pressure within the photobioreactor bag 101, one of ordinary skill in the art will recognize various other ways to control and/or vary the pressure on the exhaust end 104 of the photobioreactor bag 101, according to embodiments of the present invention. However, using submerged lines 132, 138 at different depths also provides a built-in pressure relief feature, such that an air pressure within the bag that exceeds the pressure at the submerged end 146 will simply cause excess air to flow harmlessly out of the end 146, while still maintaining the pressure (e.g. the depth) at end 146, according to embodiments of the present invention. According to some embodiments of the present invention, ports 112, 114, and/or 116, though described as single ports, may be multiple ports and/or be connected to multiple gas sources and/or multiple exhaust lines. For example, line 126 may split into two lines and may enter bag 101 at two different ports 112, one of which may be closer to end 106 than the other.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A method for harvesting algae, the method comprising:
   filling a reservoir at least partially with a liquid;
   submerging a bag at least partially in the liquid, the bag containing media, the media comprising algae, the bag comprising a first end, a second end, a harvesting port located closer to the first end than to the second end, and a gas port;
   delivering gas into the bag through the gas port; and
   raising the second end of the bag by accumulating the gas at the second end to flow the media toward the harvesting port.

2. The method of claim 1, further comprising:
   tethering the bag to the reservoir closer to the first end than to the second end.

3. The method of claim 2, wherein the bag further comprises an elongated support member, and wherein tethering the bag to the reservoir comprises tethering the elongated support member to the reservoir.

4. The method of claim 3, wherein tethering the elongated support member to the reservoir comprises pivotally coupling the elongated support member to the reservoir.

5. The method of claim 3, wherein the elongated support member is a metal pipe.

6. The method of claim 3, wherein the bag comprises a first side and a second side, the method further comprising:
   welding the first side to the second side to form a media container above the weld and a weight member interface below the weld; and
   inserting the elongated support member into the weight member interface.

7. The method of claim 1, wherein raising the second end comprises raising the second end up to an upper level of the liquid in the reservoir.

8. The method of claim 1, wherein the bag is a first bag, wherein the harvesting port is a first harvesting port, and wherein the gas port is a first gas port, the method further comprising:
   submerging a second bag at least partially in the liquid, the second bag containing media, the media comprising algae, the second bag comprising a first end, a second end, a second harvesting port located closer to the first end than to the second end, and a second gas port;
   delivering gas into the second bag through the second gas port; and
   raising the second end of the second bag by accumulating the gas at the second end to flow the media toward the second harvesting port.

9. The method of claim 8, wherein the raising of the second end of the second bag is done at a different time from the raising of the second end of the first bag.

10. The method of claim 8, wherein the first and second bags are part of a plurality of bags submerged at least partially in the liquid, and wherein the first bag is positioned adjacent to the second bag among the plurality of bags.

11. The method of claim 10, wherein the raising of the second end of the first bag and the raising of the second end of the second bag are staggered with respect to time.

12. The method of claim 1, wherein the bag is at least partially transparent, and wherein the gas comprises carbon dioxide capable of being used by the algae for photosynthesis.

13. The method of claim 2, wherein tethering the bag to the reservoir closer to the first end than to the second end comprises tethering the bag to the reservoir only at a location closer to the first end than to the second end.

14. A method for harvesting algae, the method comprising:
   submerging a bag at least partially in liquid, the bag containing media, the media comprising algae, the bag comprising a first end, a second end, a harvesting port located closer to the first end than to the second end, and a gas port;
   delivering gas into the bag through the gas port;
   raising the second end of the bag by accumulating the gas at the second end to flow the media toward the harvesting port; and
   removing the media from the bag through the harvesting port.

15. The method of claim 14, wherein removing the media from the bag through the harvesting port comprises removing the media from the bag through the harvesting port while the second end is raised above the first end.

16. The method of claim 15, wherein removing the media from the bag through the harvesting port while the second end is raised above the first end comprises removing the media from the bag through the harvesting port while the second end is raised above the first end and the harvesting port is submerged in the liquid.

17. The method of claim 14, wherein the gas and the media are in a same compartment of the bag.

18. The method of claim 14, wherein the liquid is contained by a reservoir, the method further comprising tethering the bag to the reservoir below the bag.

19. The method of claim 18, further comprising tethering the bag to the reservoir closer to the first end than to the second end.

20. The method of claim 19, further comprising pivotally coupling the bag to the reservoir.

* * * * *